US012648727B2

(12) United States Patent
Zhao et al.

(10) Patent No.: US 12,648,727 B2
(45) Date of Patent: Jun. 9, 2026

(54) WEARABLE DEVICE

(71) Applicant: HUAWEI TECHNOLOGIES CO., LTD., Shenzhen (CN)

(72) Inventors: Menglong Zhao, Xi'an (CN); Xiaogang Liu, Xi'an (CN)

(73) Assignee: Huawei Technologies Co., LTD., Shenzhen (CN)

( * ) Notice: Subject to any disclaimer, the term of this patent is extended or adjusted under 35 U.S.C. 154(b) by 350 days.

(21) Appl. No.: 18/574,888

(22) PCT Filed: Apr. 21, 2022

(86) PCT No.: PCT/CN2022/088234
§ 371 (c)(1),
(2) Date: Dec. 28, 2023

(87) PCT Pub. No.: WO2023/273541
PCT Pub. Date: Jan. 5, 2023

(65) Prior Publication Data
US 2025/0134396 A1     May 1, 2025

(30) Foreign Application Priority Data

Jun. 30, 2021     (CN) .......................... 202110731338.4

(51) Int. Cl.
| | |
|---|---|
| *A61B 5/256* | (2021.01) |
| *A61B 5/00* | (2006.01) |
| *A61B 5/01* | (2006.01) |
| *A61B 5/0205* | (2006.01) |
| *A61B 5/259* | (2021.01) |
| *A61B 5/28* | (2021.01) |

(52) U.S. Cl.
CPC .......... *A61B 5/256* (2021.01); *A61B 5/02055* (2013.01); *A61B 5/259* (2021.01); *A61B 5/28* (2021.01); *A61B 2562/0215* (2017.08)

(58) Field of Classification Search
CPC ..... A61B 5/02055; A61B 5/256; A61B 5/259; A61B 5/28; A61B 5/381; A61B 5/681; A61B 5/6838; A61B 2560/012; A61B 2560/0468
See application file for complete search history.

(56) References Cited

U.S. PATENT DOCUMENTS

2021/0353226 A1*  11/2021  Hiemstra ........... A61B 5/14552

FOREIGN PATENT DOCUMENTS

| CN | 111631706 A | 9/2020 |
|---|---|---|
| CN | 111973174 A | 11/2020 |
| WO | WO-2021254382 A1 * | 12/2021 ............. A61B 18/00 |

* cited by examiner

*Primary Examiner* — Eun Hwa Kim
(74) *Attorney, Agent, or Firm* — Fish & Richardson P.C.

(57) ABSTRACT

An example wearable device includes a first housing, a second housing, a first electrocardiograph (ECG) electrode, a circuit board, and a temperature sensor. The first housing includes a first surface, a second surface. The circuit board is disposed with a contact. The first ECG electrode includes a first detection end, a second detection end, and a connection part. The first detection end is disposed on the first surface, the second detection end is disposed on the second surface. The second detection end is electrically connected to the contact and is in thermally conductive contact with the temperature sensor.

12 Claims, 11 Drawing Sheets

1a(1)

1a(1)

1

102

2a

1a

1c

1b

101

1011

201 4 103 203(2a) 202 6 5 1 3

WEARABLE DEVICE

CROSS-REFERENCE TO RELATED APPLICATIONS

This application is a national stage of International Application No. PCT/CN2022/088234, filed on Apr. 21, 2022, which claims priority to Chinese Patent Application No. 202110731338.4, filed on Jun. 30, 2021. Both of the afore-mentioned applications are hereby incorporated by reference in their entireties.

TECHNICAL FIELD

This application relates to the field of electronic device technologies, and in particular, to a wearable device.

BACKGROUND

Nowadays, people pay more attention to health conditions of themselves and their families, and want health indicators to be monitored in various scenarios such as exercise, sleep, work, and daily life. With the development of science and technology, functions such as heart rate monitoring, blood oxygen saturation monitoring, electrocardiogram monitor-ing, and body temperature monitoring start to be integrated into some common electronic devices.

An intelligent wearable product (for example, a smart watch or a smart band) has been popular with a large quantity of consumers in recent years due to advantages such as convenient wearing and increasingly diversified functions. For a purpose of meeting consumers' require-ments for health indicator monitoring, more functional mod-ules are integrated into a current intelligent wearable prod-uct. However, with an increase of functional modules, fineness, wearing comfort, and the like of the intelligent wearable product are affected.

Therefore, how to further meet a wearing comfort require-ment for the intelligent wearable product when diversified functions of the intelligent wearable product is implemented has become a technical problem to be urgently resolved by a person skilled in the art.

SUMMARY

This application provides a wearable device. The wear-able device may monitor body signs such as an electrocar-diogram and a body temperature of a user in real time, and integrate an electrocardiogram detection function and a body temperature detection function, to implement a miniaturiza-tion design of the wearable device and improve wearing comfort.

The wearable device provided in this application may include a housing. The housing includes a first housing and a second housing. The first housing and the second housing are disposed in a snap-fit manner, to form accommodation space between the first housing and the second housing. Modules that are of the wearable device and that are configured to implement a function of the wearable device are disposed in the accommodation space. The first housing may include a first surface, a second surface, and a first via, where the first surface and the second surface are disposed back to each other, and the second surface faces the accom-modation space. The first via may penetrate the first housing in a direction from the first surface to the second surface.

In this application, the wearable device may further include a first ECG electrode. The first ECG electrode includes a first detection end, a second detection end, and a connection part. The first detection end is disposed on the first surface of the first housing, the second detection end is disposed on the second surface of the first housing, the connection part penetrates the first via, and the first detection end is connected to the second detection end through the connection part. A circuit board is further disposed in the accommodation space of the wearable device. A contact is disposed on the circuit board. The contact may be electri-cally connected to each functional module on the circuit board. The second detection end of the first ECG electrode may be electrically connected to the contact, so that an electrical signal collected by the first ECG electrode may be transmitted to a corresponding functional module on the circuit board by using the contact, thereby implementing a corresponding function.

In addition, a temperature sensor may be further disposed on the circuit board, and the second detection end of the first ECG electrode is further in thermally conductive contact with the temperature sensor. In this way, a body temperature may be collected by using the first ECG electrode, and the body temperature may be conducted to the temperature sensor, so that body temperature measurement is imple-mented by the wearable device.

According to the wearable device provided in this appli-cation, an electrical signal and a temperature signal may be collected and transmitted by using the first ECG electrode, and a plurality of functions of the wearable device may be integrated, to effectively save space for disposing modules configured to implement corresponding functions. This helps implement a design for miniaturization and thinning of the wearable device. In addition, implementations of the plurality of functions are integrated by using the first ECG electrode, so that space may be reserved for setting more functional modules of the wearable device, thereby facili-tating implementation of a design of diversified functions of the wearable device and improving user experience.

To implement collecting the electrical signal and the temperature signal by the first ECG electrode, in a possible implementation of this application, the first ECG electrode may include a substrate and a filler that is doped on the substrate and that has a thermally and electrically conductive property. The substrate may be but is not limited to a resin material substrate, and the filler may be but is not limited to silicon carbide or silver.

In addition, a thermally and electrically conductive adhe-sive may be further disposed between the second detection end of the first ECG electrode and the circuit board, so that the second detection end may be electrically connected to the contact on the circuit board through the thermally and electrically conductive adhesive. In a possible implementa-tion of this application, the second detection end may be further in thermally conductive contact with the temperature sensor through the thermally and electrically conductive adhesive, thereby simplifying a structure of the wearable device.

It can be learned from the foregoing description that the contact on the circuit board may be electrically connected to each functional module on the circuit board, to implement a corresponding function. In a possible implementation of this application, the contact may be a first-type contact. In addition, an ECG module is disposed on the circuit board, and the first-type contact is electrically connected to the ECG module. In this way, when the second detection end of the first ECG electrode is electrically connected to the first-type contact, an electrocardiogram detection function of the wearable device can be implemented.

In another possible implementation of this application, the contact may alternatively be a second-type contact, an antenna module may be further disposed on the circuit board, and the second-type contact may be electrically connected to the antenna module. The second detection end of the first ECG electrode is electrically connected to the second-type contact, so that a wireless signal may be transmitted and received by using the first ECG electrode, thereby implementing a wireless communication function between the wearable device and an external terminal device.

A charging pin may be further disposed on the circuit board, and the charging pin may be electrically connected to the second detection end. In addition, a charging module may be further disposed on the circuit board, and the charging pin may be electrically connected to the charging module. In this way, the first ECG electrode may be electrically connected to an external charging device, and a charging current may be transferred to the charging module through the charging pin, to implement a charging function of the wearable device.

In this application, a material of the first housing may be but is not limited to glass, ceramic, plastic, or the like. In a possible implementation, the first housing may be an integrally formed structure, to improve appearance aesthetics of the wearable device.

In another possible implementation of this application, the first housing may alternatively be an assembly structure. During specific implementation, the first housing may include a fastening part and a detection part, the fastening part is provided with a mounting hole, the detection part is mounted in the mounting hole, and the detection part is fastened. In this implementation, the first ECG electrode may be disposed on the detection part. In addition, the detection part may alternatively be a protruding structure that is opposite to the fastening part and that faces away from the accommodation space, to implement stable contact between the first ECG electrode and the detection part.

In a possible implementation of this application, a second ECG electrode may be disposed on the second housing. The second housing includes a display, the display has a first surface and a second surface, the first surface and the second surface are disposed back to each other, and the second surface faces the accommodation space. In this case, the second ECG electrode may be disposed on the display, and a second via that penetrates from the first surface to the second surface may be disposed on the display. In this case, the second ECG electrode may pass through the via and extend from the first surface to the second surface of the display, and a part that is of the second ECG electrode and that is located on the first surface of the display is electrically connected to a part that is of the second ECG electrode and that is located on the second surface of the display. Based on the foregoing descriptions of integrating implementations of the plurality of functions on the first housing side by using the first ECG electrode, the part that is of the second ECG electrode and that is located on the second surface of the display may also be electrically connected to the contact on the circuit board in the accommodation space. In addition, besides the foregoing first-type contact, the contact may further include the second-type contact. The antenna module is disposed on the circuit board, the second-type contact may be electrically connected to the antenna module, and the second ECG electrode may be electrically connected to the second-type contact. In this way, an antenna signal may be received or transmitted by using the part that is of the second ECG electrode and that is disposed on the first surface of the display, to implement an antenna function of the wearable device.

In addition, in this application, the part that is of the second ECG electrode and that is located on the second surface may be further in thermally conductive contact with the temperature sensor on the circuit board, or may be electrically connected to the charging pin on the circuit board, and may be properly disposed, so that an electrocardiogram detection function, a body temperature detection function, a charging function, and an antenna function are integrated by using the second ECG electrode on the display.

In addition to the foregoing structure, the second housing may further include a support. The support is located on a side that is of the display and that faces the accommodation space. The display may be fastened on the support, so that the support supports the display. The support has a side wall, and the side wall may be configured to connect the first housing and the display, so that the side wall, the first housing, and the display jointly form the accommodation space. In a possible implementation of this application, a third ECG electrode may be disposed on the support, and the third ECG electrode may be disposed on the side wall of the support. The side wall may include a first surface and a second surface, the first surface and the second surface are disposed back to each other, and the second surface faces the accommodation space. A third via that penetrates from the first surface to the second surface may be disposed on the side wall, and the third ECG electrode may extend from the first surface to the second surface of the side wall. Based on the foregoing descriptions of integrating implementations of the plurality of functions on the first housing side by using the first ECG electrode, a part that is of the third ECG electrode on the side wall and that is located on the second surface may also be electrically connected to the contact on the circuit board in the accommodation space, and in thermally conductive contact with the temperature sensor. In addition, the electrocardiogram detection, the body temperature detection, the charging function, the antenna function, and the like are integrated by using the third ECG electrode on the side wall of the support through proper setting.

REFERENCE NUMERALS

1: first housing; 1*a*: first surface of the first housing; 1*b*: second surface of the first housing; 1*c*: side surface; 101: fastening part;

1011: mounting hole; 102: detection part; 103: via; 2*a*, 2*b*, and 2*c*: ECG electrode; 201: first detection end;

202: second detection end; 203: connection part; 3: circuit board; 4: contact; 5: thermally and electrically conductive adhesive; 6: temperature sensor;

7: charging pin; 8: second housing; 81: display; 81*a*: first surface of the display; 81*b*: second surface of the display;

8101: via; 82—support; 82*a*: first surface of the support; 82*b*: second surface of the support; 8201: via; and

9: mounting bracket.

DESCRIPTION OF EMBODIMENTS

For ease of understanding of a wearable device provided in embodiments of this application, the following first describes an application scenario of the wearable device. The wearable device provided in this application may be used for health monitoring of a human body. A wearable device that has a function of monitoring human health, such as a smart watch or a smart band, is one of important mobile and online health monitoring products, and is widely praised by users. Therefore, the wearable device provided in this application may be, but is not limited to, a portable electronic device such as a smart watch or a smart band.

A smart watch is used as an example. The smart watch may be usually worn on a wrist of a user. In this way, an electrocardiograph (electrocardiograph, ECG) may be disposed on the smart watch, to conveniently detect an electrocardiogram of a human body. Human body indicators such as a heart rate, a heart rate variability (heart rate variability, HRV), and blood pressure may be obtained by calculating an electrocardiogram obtained through ECG measurement. In this way, a physical state can be predicted, to effectively avoid a conduction system disorder of a heart or a myocardial lesion. In addition, a body temperature is also an important health indicator of the human body, and a health state of the body can also be predicted by measuring the body temperature of the human body, thereby effectively reducing a risk of occurrence of a dangerous disease.

In a current wearable device such as a smart watch, both an ECG module and a body temperature measurement module are usually disposed. Because detection of the electrocardiogram and the body temperature usually requires contact with human body skin, the ECG module and the body temperature measurement module may be disposed on a side that is of the wearable device and that is in contact with the human body.

Figure 1:
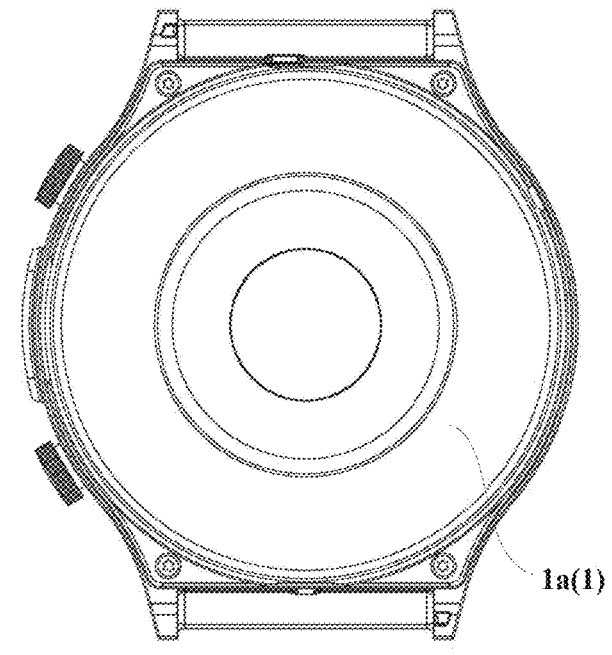
FIG. 1 is a schematic diagram of a structure of a wearable device according to an embodiment of this application.

FIG. 1 is a schematic diagram of a structure of a wearable device according to an embodiment of this application. The wearable device may include a housing, and the housing has a first housing and a second housing. The first housing 1 and the second housing are disposed back to each other. In addition, the first housing 1 and the second housing are disposed in a snap-fit manner, to form, between the first housing 1 and the second housing, accommodation space used to accommodate functional modules of the wearable device. In this application, when the wearable device is worn, the first housing 1 may be in contact with the human body, and the ECG module and the body temperature measurement module may be disposed close to the first housing 1.

Figure 2:
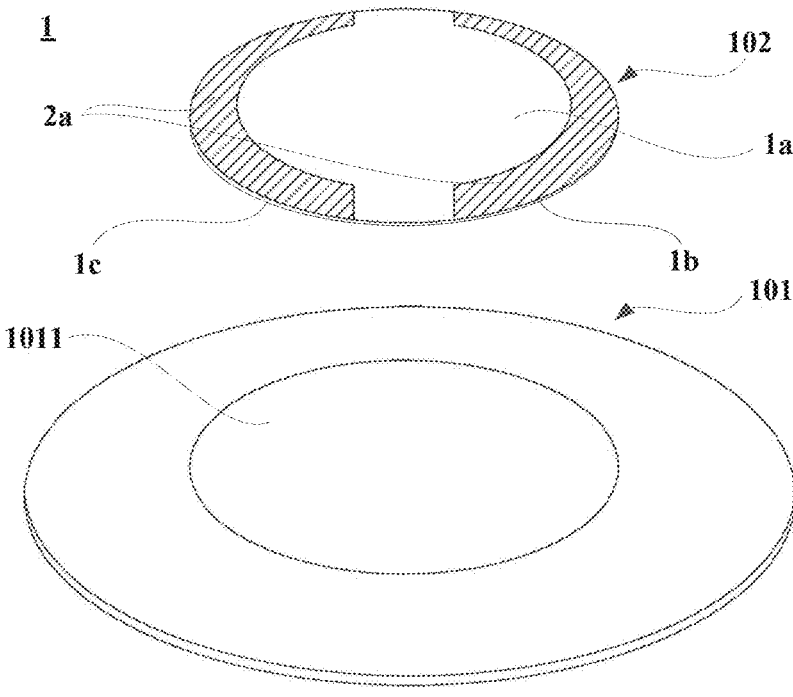
FIG. 2 is an exploded view of a first housing of a wearable device according to an embodiment of this application.

FIG. 2 is an exploded view of a first housing 1 of an existing wearable device according to an embodiment of this application. In this application, for ease of description, a side surface that is of the first housing 1 and that is used to contact the human body may be defined as a first surface 1*a* of the first housing 1, and a side surface that is of the first housing 1 and that faces the accommodation space is defined as a second surface 1*b* of the first housing 1. The first surface 1*a* and the second surface 1*b* are disposed back to each other. In addition, a connection surface that is of the first housing 1 and that is used to connect the first surface 1*a* and the second surface 1*b* may be further defined as a side surface 1*c* of the first housing 1.

Still with reference to FIG. 2, in this embodiment, the first housing 1 includes a fastening part 101 and a detection part 102. The fastening part 101 may be provided with a mounting hole 1011. For example, the fastening part 101 may be of an annular structure. The detection part 102 may be mounted in the mounting hole 1011 of the fastening part 101, and the detection part 102 is fastened to the fastening part 101. In this embodiment of this application, a material of the fastening part 101 may be plastic, ceramic, glass, or the like, a material of the detection part 102 may be plastic, ceramic, glass, or the like, and materials of the fastening part 101 and the detection part 102 may be the same or may be different.

The ECG module may usually include an ECG electrode 2*a*. In the embodiment shown in FIG. 2, the ECG electrode 2*a* may be disposed on the first surface 1*a* of the first housing 1, and the ECG electrode 2*a* is disposed along an edge of the first surface 1*a*. In addition, wiring may be performed on the side surface 1*c* of the first housing 1, to lead the ECG electrode 2*a* disposed on the first surface 1*a* to the second surface, so that the ECG electrode 2*a* may be electrically connected to a part that is of the ECG module and that is disposed in the accommodation space.

In addition, in the embodiment shown in FIG. 2, when the body temperature measurement module is specifically disposed, a structure such as a thermally conductive column (not shown in the figure) may be embedded in the fastening part 101, to conduct the detected human body temperature through the thermally conductive column to a part of the body temperature measurement module located in the accommodation space, thereby implementing body temperature measurement.

Figure 3:
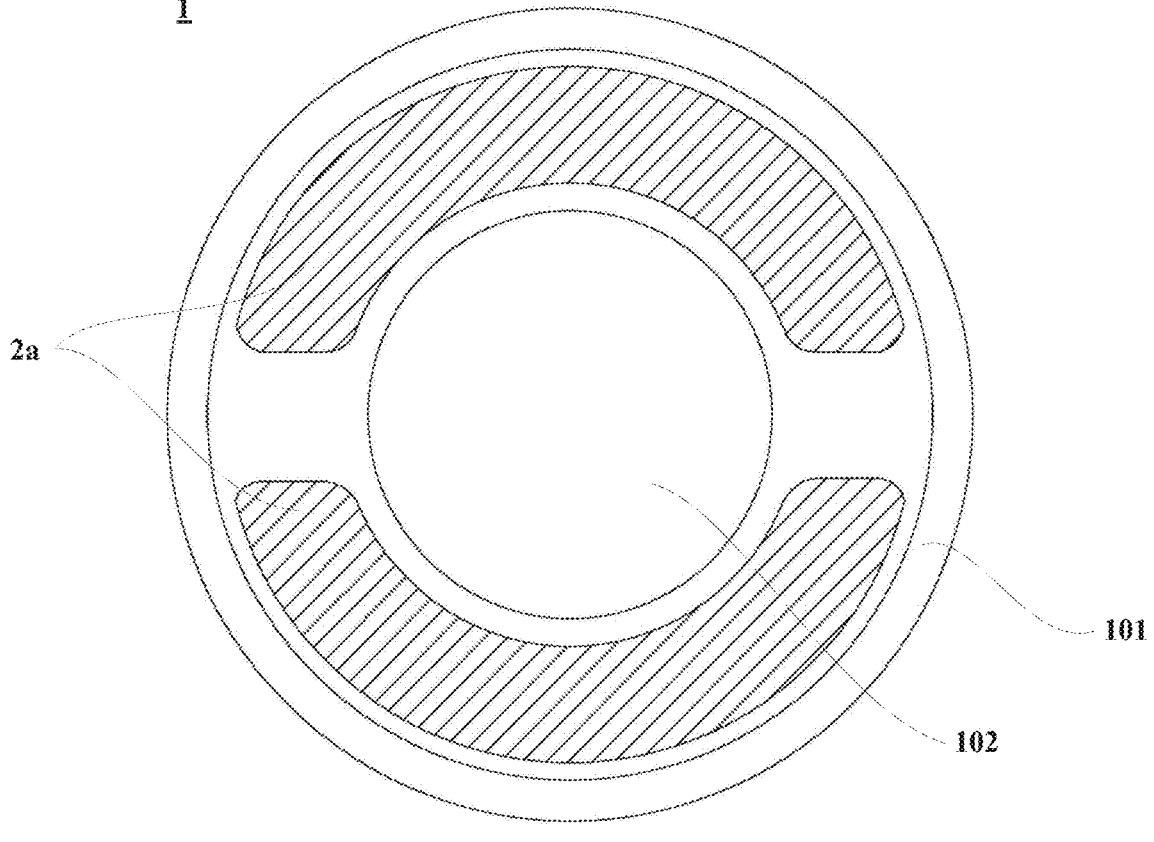
FIG. 3 is a schematic diagram of a structure of a first housing of a wearable device according to another embodiment of this application.

FIG. 3 is a schematic diagram of a structure of a first housing 1 of an existing wearable device according to another embodiment of this application. In the embodiment, the ECG electrode 2*a* may be embedded in the fastening part 101, and the ECG electrode 2*a* may be extended to the accommodation space and electrically connected to another part of the ECG module. Different from the foregoing embodiment, in the embodiment shown in FIG. 3, the detection part 102 may be made of sapphire glass with a relatively high thermal conductivity, and the body temperature detected by the sapphire glass may be conducted to the part of the body temperature measurement module located in the accommodation space, thereby implementing the body temperature measurement.

It can be learned from the foregoing embodiments shown in FIG. 2 and FIG. 3 that, in an existing wearable device that has both an electrocardiogram detection function and a body temperature detection function, the ECG module and the body temperature measurement module need to be separately disposed, and occupy relatively large space in the wearable device. Therefore, a design requirement for miniaturization and thinning of the wearable device is affected.

The wearable device provided in this application is intended to resolve the foregoing problem, to save space for disposing modules configured to implement the electrocardiogram detection function and the body temperature detection function by integrating the ECG module and the body temperature measurement module. This helps implement the design for miniaturization and thinning of the wearable device. In addition, space may be further reserved for setting another functional module, to increase function diversity of the wearable device.

To make objectives, technical solutions, and advantages of this application clearer, the following further describes this application in detail with reference to the accompanying drawings and specific embodiments.

Terms used in the following embodiments are only intended to describe specific embodiments, but are not intended to limit this application. As used in this specification and appended claims of this application, singular expressions "one", "a", "the foregoing", "the", and "the one" are also intended to include expressions such as "one or more", unless the contrary is clearly indicated in the context. It should be further understood that in the following embodiments of this application, "at least one" and "one or more" refer to one, two, or more. The term "and/or" is used to describe an association relationship between associated objects and represents that three relationships may exist. For example, A and/or B may represent the following cases: Only A exists, both A and B exist, and only B exists, where A and B may be singular or plural. The character "/" usually indicates an "or" relationship between the associated objects.

Reference to "an embodiment", "some embodiments", or the like described in this specification indicates that one or more embodiments of this application include a specific feature, structure, or characteristic described with reference to the embodiment. Therefore, statements such as "in an embodiment", "in some embodiments", "in some other embodiments", and "in other embodiments" that appear at different places in this specification do not necessarily refer to a same embodiment. Instead, the statements mean "one or more but not all of embodiments", unless otherwise specifically emphasized in another manner. The terms "include", "comprise", and "have", and variants thereof all mean "include but are not limited to", unless otherwise specifically emphasized in another manner.

Figure 4:
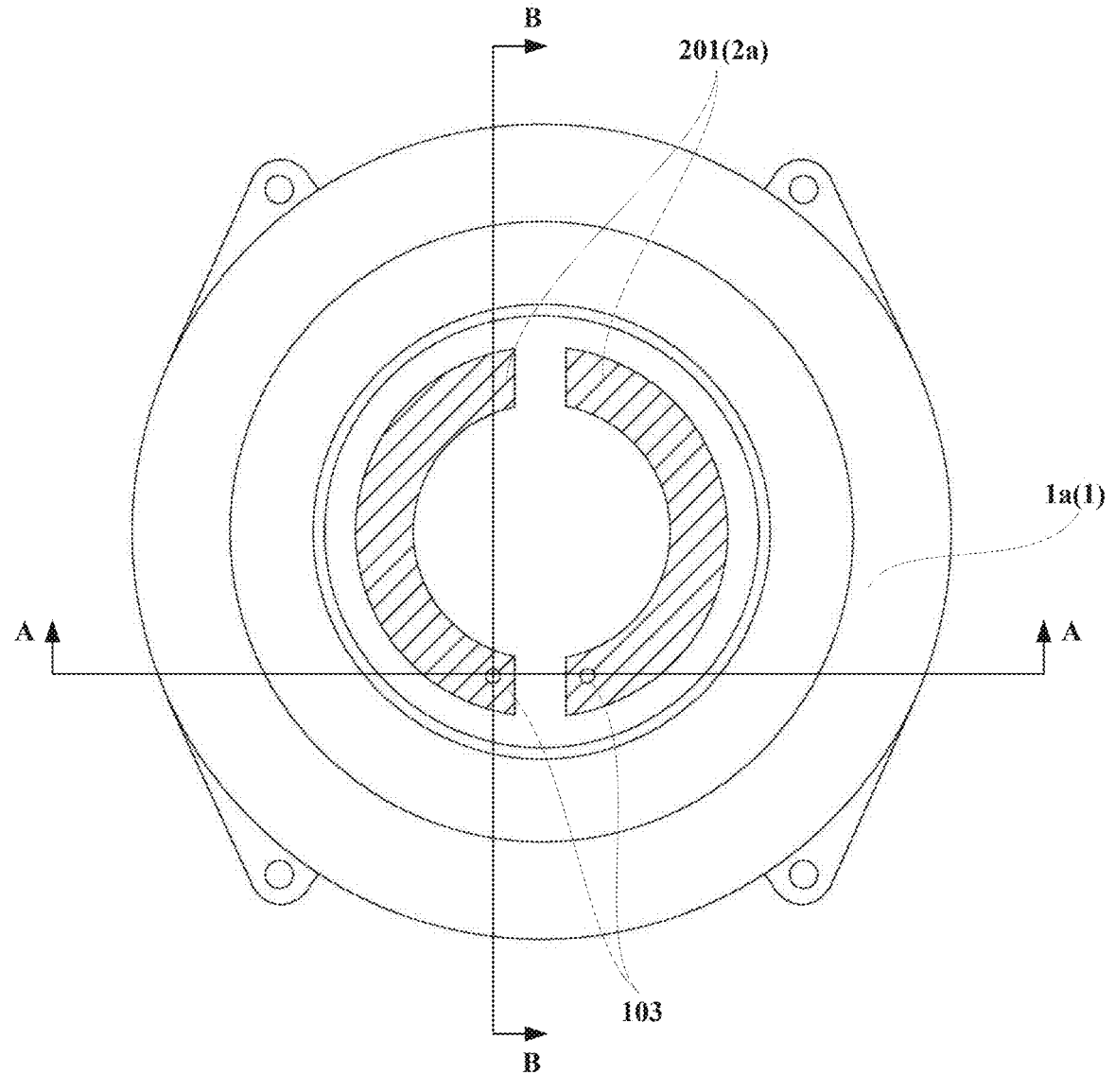
FIG. 4 is a schematic diagram of a structure of a wearable device according to another embodiment of this application.

FIG. 4 is a schematic diagram of a structure of a wearable device according to a possible embodiment of this application. In this embodiment, the first housing 1 of the wearable device may be an integrally formed structure. A material of the first housing 1 may be but is not limited to ceramic, glass, plastic, or the like. The first housing 1 is disposed as an integrally formed structure, so that structural reliability of the first housing 1 can be effectively improved, thereby improving structural stability of the entire wearable device. In addition, the first housing 1 is disposed in an integrated manner, so that an integration degree of the wearable device can be further improved, thereby improving appearance aesthetics of the wearable device.

In the embodiment shown in FIG. 4, the ECG electrode 2a is disposed on the wearable device, and the ECG electrode 2a may be disposed on the first surface 1a of the first housing 1. In this application, the ECG electrode 2a may include, but is not limited to, a material that has a thermally and electrically conductive property, such as silicon carbide or silver. In a possible embodiment of this application, the ECG electrode 2a may include a resin material substrate, and a filler that is doped on the resin material substrate and that has a thermally and electrically conductive property, such as silicon carbide or silver, so that the ECG electrode 2a can be configured to transmit both an electrical signal and a temperature signal. In addition, the ECG electrode 2a may be formed on the first surface 1a of the first housing 1 through physical vapor deposition (physical vapor deposition, PVD), printing, slurry sintering, or the like.

Still with reference to FIG. 4, a shape of the ECG electrode 2a is not specifically limited in this application. For example, the ECG electrode 2a may be set to an are shown in FIG. 4, or may be set to another regular shape such as a circle or a square, or may be set to some possible irregular shapes. In addition, there may be one or more ECG electrodes 2a. For example, when there are two ECG electrodes 2a, both the two ECG electrodes 2a may be disposed in arcs shown in FIG. 4, and the two arcs are symmetrically disposed, to improve aesthetics of disposing the ECG electrodes 2a. In some other possible embodiments of this application, when there are a plurality of ECG electrodes 2a, shapes of the plurality of ECG electrodes 2a may be different, and the plurality of ECG electrodes 2a may be designed based on space that is of the first surface 1a of the first housing 1 and that can be used to dispose the ECG electrodes 2a. It may be understood that the plurality of ECG electrodes 2a are disposed on the first surface 1a of the first housing 1, so that multi-point measurement can be implemented. This can effectively improve stability and reliability of the electrocardiogram detection and body temperature detection, thereby helping improve accuracy of the electrocardiogram detection and body temperature detection.

In addition, the ECG electrode 2a may be disposed at any position on the first surface 1a. For example, the ECG electrode 2a may be disposed in a central region of the first surface 1a. According to the wearable device provided in this solution, there is no requirement on a position at which the ECG electrode 2a is disposed on the first surface 1a, and this can effectively reduce process control difficulty of the ECG electrode 2a. In a possible embodiment of this application, a region that is on the first surface 1a and that is used to dispose the ECG electrode 2a may further protrude towards a direction away from the accommodation space, so that the ECG electrode 2a is in reliable contact with the human body.

Still with reference to FIG. 4, a via 103 is further disposed on the first housing 1, and the via 103 penetrates the first housing 1 in a direction from the first surface 1a to the second surface. In this application, a manner of forming the via 103 may be but is not limited to computerized numerical control (computerized numerical control, CNC), laser drilling, or direct forming through a molding process. The ECG electrode 2a covers the via 103. It may be understood from the descriptions of the forming process of the ECG electrode 2a in the foregoing embodiment that, in a process of forming the ECG electrode 2a through the PVD, a part of a material used to form the ECG electrode 2a may spread through the via 103 to the second surface of the first housing 1.

A specific shape of the via 103 is not limited in this application. For example, the via 103 may be a regular hole such as a circle, a square, or a triangle, or may be some possible irregular holes. In addition, it may be understood that a smaller aperture of the via 103 has less impact on an appearance effect of the first housing 1, and it is easier to meet a waterproof property requirement of the first housing 1. However, an aperture of the via 103 is excessively small, which is not conducive for the material used to form the ECG electrode 2a to pass through the via 103. In a possible embodiment of this application, the aperture of the via 103 may be 0.1 mm to 5 mm. For example, the aperture may be 0.2 mm, 0.5 mm, 0.7 mm, 1.0 mm, 3 mm, or the like. Therefore, a waterproof design of the first housing 1 is easily implemented on the basis of satisfying the appearance effect of the first housing 1.

Figure 5:
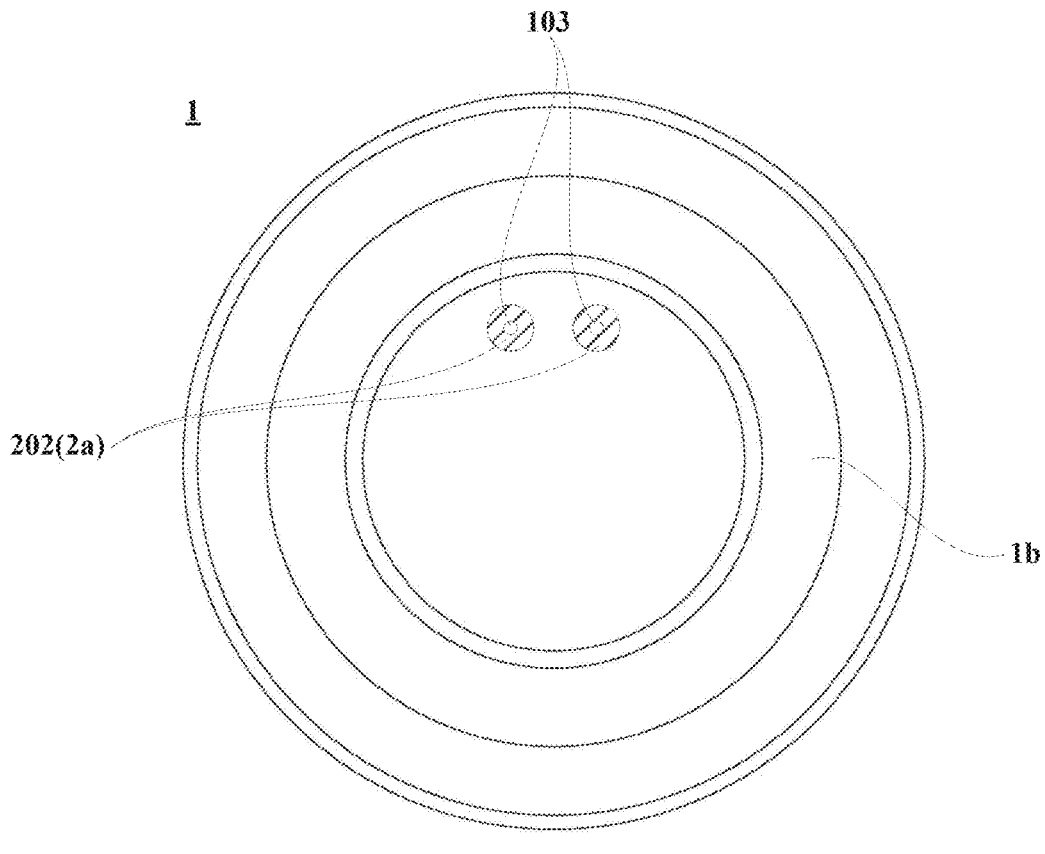
FIG. 5 is a schematic diagram of a structure of a second surface of a first housing of a wearable device according to an embodiment of this application.

FIG. 5 is a schematic diagram of a structure of a second surface 1b of a first housing 1 according to an embodiment of this application. It may be understood that, in this application, the material of the ECG electrode 2a may fill the entire via 103 to block the via 103, or may be formed only on a hole wall of the via 103 as long as a part of the ECG electrode 2a formed on the first surface 1a and a part of the ECG electrode 2a formed on the second surface 1b can be connected. For ease of description, in this application, a part that is of the ECG electrode 2a and that is located on the first surface 1a may be referred to as a first detection end 201, a part that is of the ECG electrode 2a and that is located on the second surface 1b is referred to as a second detection end 202, and a part that is of the ECG electrode 2a and that penetrates into the via 103 is referred to as a connection part. It may be understood that the first detection end 201 and the second detection end 202 are connected through the connection part.

Still with reference to FIG. 5, a shape of the second detection end 202 is not specifically limited in this application. For example, the shape may be a circle shown in FIG. 5. In some other embodiments, the shape may be a regular shape such as an ellipse, a triangle, or a rectangle, or may be some possible irregular shapes. In addition, an area of the second detection end 202 is not limited in this application. For example, the area of the second detection end 202 may be greater than a cross-sectional area of the via 103, so that the second detection end 202 is electrically connected to another device located in the accommodation space of the wearable device, and the entire ECG electrode 2a is electrically connected to the another device located in the accommodation space of the wearable device.

It can be learned from the descriptions of the foregoing embodiment that, in this application, there may be a plurality of ECG electrodes 2a, and the via 103 may be disposed for each corresponding ECG electrode 2a, to implement an electrical connection between each ECG electrode 2a and the another device located in the accommodation space of the wearable device. In addition, a quantity of vias 103 disposed corresponding to each ECG electrode 2a may be the same or may be different, and may be specifically disposed based on a connection relationship between the ECG electrode 2a and a device in the accommodation space of the wearable device.

Figure 6:
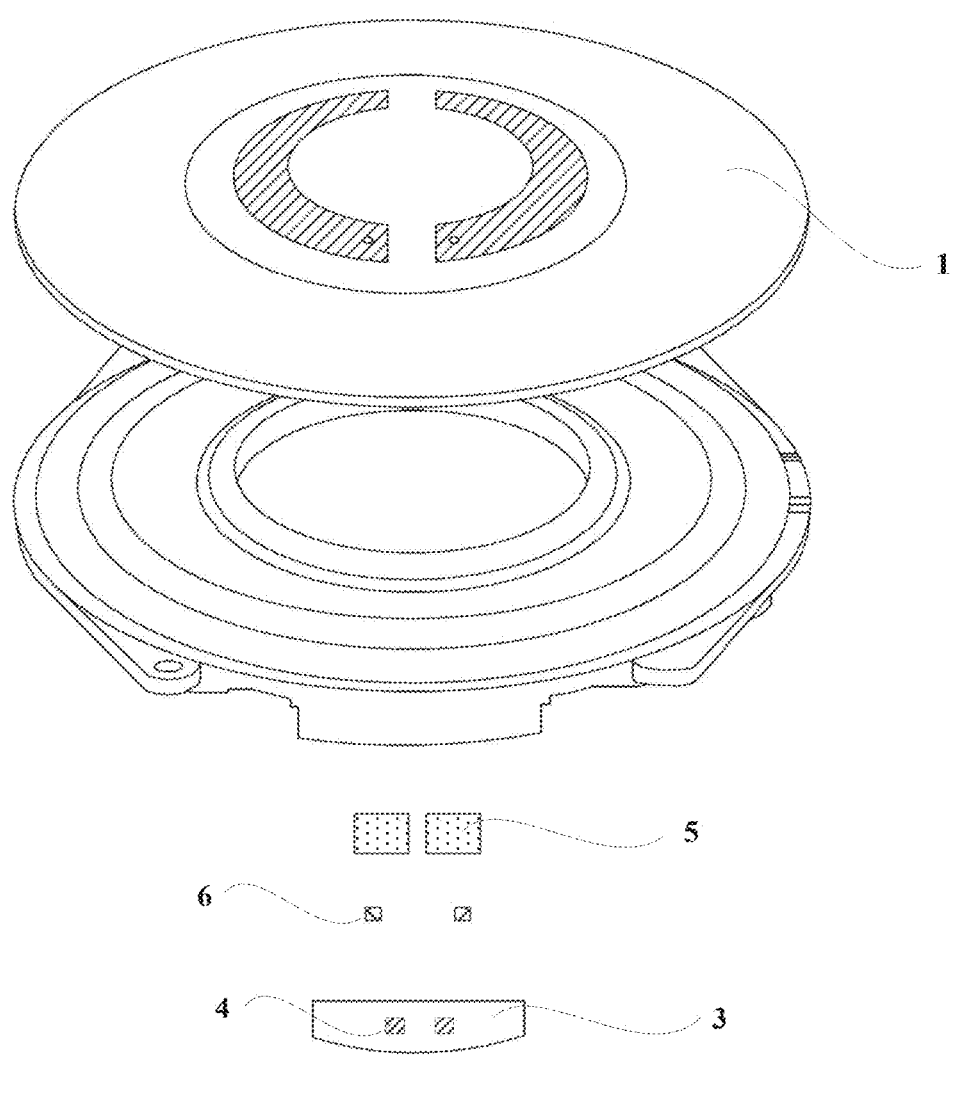
FIG. 6 is an exploded view of a partial structure of a wearable device according to an embodiment of this application.

To implement functions of electrocardiogram detection and body temperature detection of the wearable device, the wearable device provided in this application may further include a circuit board 3. FIG. 6 is an exploded view of a partial structure of a wearable device according to an embodiment of this application. In this embodiment, the circuit board 3 may be disposed in the accommodation space of the wearable device. For example, the circuit board 3 may be a printed circuit board (printed circuit board, PCB) or a flexible printed circuit (flexible printed circuit, FPC). The circuit board 3 may integrate the ECG module and the body temperature measurement module, such as a functional module, a control module, a processing module, a storage module, or the like that are configured to implement the electrocardiogram detection and body temperature detection.

A metal wire is usually disposed in the circuit board 3, and each metal wire may be electrically connected to the corresponding modules integrated in the circuit board 3. Still with reference to FIG. 6, a contact 4 is further disposed on the circuit board 3. In a possible embodiment of this application, a part that is of the metal wire and that is formed on a surface of the circuit board 3 may be used as the contact 4. Alternatively, a covering on the surface of the circuit board 3 is etched off to expose a corresponding metal wire, so that an exposed part of the metal wire is used as the contact 4. In this way, the contact 4 can be electrically connected to the metal wire, so that the contact 4 can be electrically connected to various modules.

It may be understood that the foregoing manner of disposing the contact 4 is merely an example description provided in some possible embodiments of this application. In some other embodiments of this application, the contact 4 may be alternatively set in another possible manner. Details are not listed herein.

Figure 7:
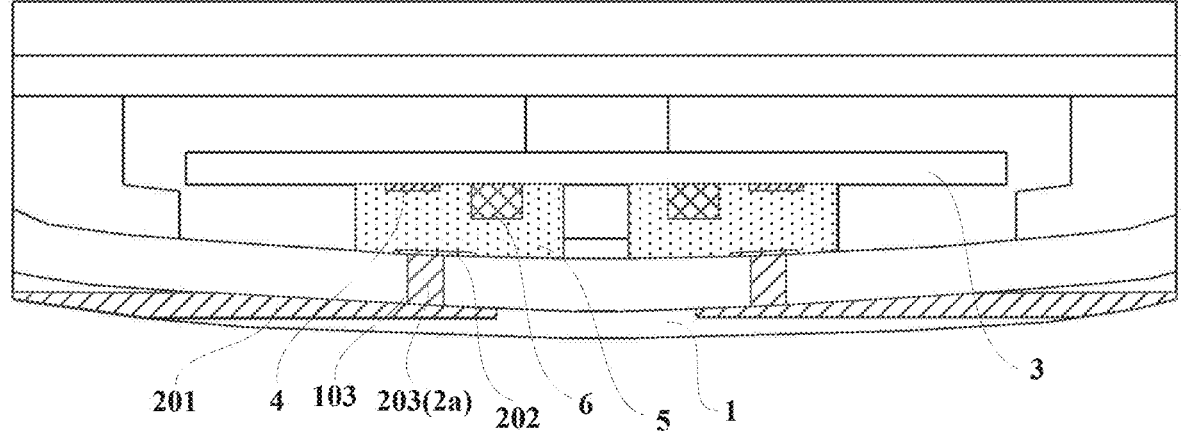
FIG. 7 is a cross-sectional view along A-A in FIG. 4.

In this application, the contact 4 may be electrically connected to the ECG module in the circuit board 3. In this way, the second detection end 202 of the ECG electrode 2a shown in FIG. 5 may be electrically connected to the contact 4, to implement an electrical connection between the entire ECG electrode 2a and the circuit board 3. In specific implementation, refer to FIG. 7. FIG. 7 is a cross-sectional view along A-A in FIG. 4. In this embodiment, a thermally and electrically conductive adhesive 5 may be disposed between the second detection end 202 of the ECG electrode 2a and the contact 4, to electrically connect the second detection end 202 to the contact 4 through the thermally and electrically conductive adhesive 5. It may be understood that, when the second detection end 202 and the contact point 4 are connected through the thermally and electrically conductive adhesive 5, the thermally and electrically conductive adhesive 5 may further block the via 103, to seal the via 103, thereby implementing a waterproof effect of the entire first housing 1.

In the foregoing embodiment, a manner of electrical connection between the second detection end 202 and the contact 4 is merely an example description provided in this application. In some other possible embodiments of this application, the second detection end 202 may be electrically connected to the contact 4 through a lead, a spring, or another possible structure having a thermally and electrically conductive property. In addition, the via 103 may also be waterproofed and sealed by applying a waterproof glue.

Because the thermally and electrically conductive adhesive 5 has a relatively good thermally and electrically conductive property, in addition to transmitting an electrical signal collected by the ECG electrode 2a to the contact 4, the thermally and electrically conductive adhesive 5 may also transmit a temperature collected by the ECG electrode 2a to the circuit board 3. In addition, because the ECG electrode 2a is also formed by using a material having a thermally and electrically conductive property, in some possible embodiments of this application, the ECG electrode 2a and the thermally and electrically conductive adhesive 5 may include a same material having a thermally and electrically conductive property, to improve efficiency of performing electrical signal transmission and temperature conduction by the ECG electrode 2a by using the thermally and electrically conductive adhesive 5. In some other embodiments of this application, the ECG electrode 2a is different from a material that has a thermally and electrically conductive property in the thermally and electrically conductive adhesive 5, provided that the ECG electrode 2a may perform the electrical signal transmission and temperature conduction by using the thermally and electrically conductive adhesive 5.

With reference to both FIG. 6 and FIG. 7, in this application, a temperature sensor 6 may be further disposed on the circuit board 3, and the temperature sensor 6 is electrically connected to the circuit board 3. In this application, an electrical connection between the temperature sensor 6 and the circuit board 3 may be implemented through an electrical connection between the temperature sensor 6 and the metal wire in the circuit board 3. In addition, the temperature sensor 6 may be fastened to the circuit board 3, and a fastening manner of the temperature sensor 6 may be but is not limited to welding or bonding.

Still with reference to FIG. 7, in this application, the second detection end 202 of the ECG electrode 2a may further be in thermally conductive contact with the temperature sensor 6, and a contact manner may be direct contact or indirect contact. In a possible embodiment of this application, the thermally and electrically conductive adhesive 5 may be further disposed between the temperature sensor 6 and the second detection end 202, and the second detection end 202 is connected to the temperature sensor 6 through the thermally and electrically conductive adhesive 5. It may be understood that the thermally and electrically conductive adhesive 5 may further have a bonding property. In this way, the temperature sensor 6 may be bonded and fastened to the circuit board 3 through the thermally and electrically conductive adhesive 5.

In the wearable device provided in this application, the ECG electrode 2a may extend from the first surface 1a of the first housing 1 to the second surface 1b of the first housing 1 through the via 103 that penetrates the first housing 1. In addition, the ECG electrode 2a is formed by using the material having a thermally and electrically conductive property, and the second detection end 202 of the ECG electrode 2a is electrically connected to the contact 4 on the circuit board 3 through the thermally and electrically conductive adhesive 5. In this way, an electrocardiogram electrical signal detected by the ECG electrode 2a may be transmitted to the contact 4 by using the thermally and electrically conductive adhesive 5, and the BCG module connected to the contact 4 analyzes and processes the electrocardiogram electrical signal, to obtain corresponding electrocardiogram data, thereby implementing the electrocardiogram detection of the human body. In addition, the second detection end 202 of the ECG electrode 2a is connected to the temperature sensor 6 on the circuit board 3 through the thermally and electrically conductive adhesive 5. In this case, a temperature signal collected by the first detection end 201 of the ECG electrode 2a may be conducted to the second detection end 202 by using the connection part 203 disposed in the via 103, and is conducted to the temperature sensor 6 by using the thermally and electrically conductive adhesive 5. Then, the temperature signal is analyzed and processed by using the body temperature measurement module that is integrated in the circuit board 3 and that is configured to implement the temperature detection, to obtain temperature data of the human body, thereby implementing the body temperature detection of the human body.

According to the wearable device provided in this embodiment of this application, functions of electrocardiogram detection and body temperature detection may be integrated by using the ECG electrode 2a having a thermally and electrically conductive property, thereby effectively saving the space for disposing the modules configured to implement the electrocardiogram detection function and the body temperature detection function. This helps implement the design for miniaturization and thinning of the wearable device. In addition, the electrocardiogram detection function and the body temperature detection function are integrated, so that space may be reserved for setting another functional module of the wearable device, thereby facilitating implementation of a design of diversified functions of the wearable device and improving user experience.

Figure 8:
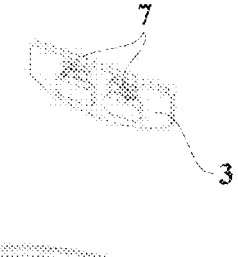
FIG. 8 is an exploded view of a partial structure of a wearable device according to another embodiment of this application.
Figure 8:
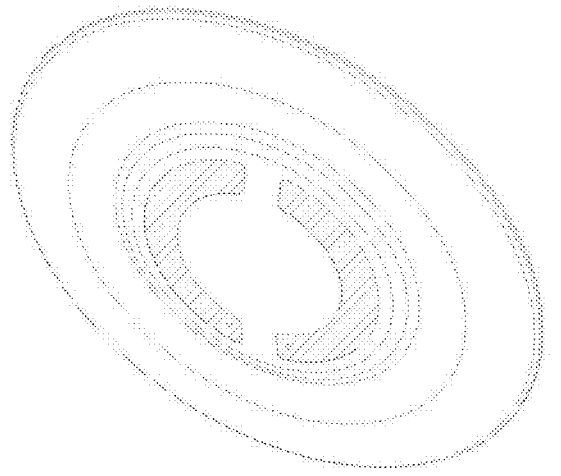

It can be learned from the descriptions of the foregoing embodiment that the ECG electrode 2a is formed by using the material having a thermally and electrically conductive property. In a possible embodiment of this application, a charging function of the wearable device may be further integrated into the ECG electrode 2a. In specific implementation, refer to FIG. 8. FIG. 8 is an exploded view of a partial structure of a wearable device according to an embodiment of this application. In this embodiment, a charging pin 7 may be further disposed on the circuit board 3, and the charging pin 7 is electrically connected to the circuit board 3. In this application, an electrical connection between the charging pin 7 and the circuit board 3 may be implemented through an electrical connection between the charging pin 7 and a metal wire in the circuit board 3. In addition, the metal wire electrically connected to the charging pin 7 in the circuit board 3 may also be electrically connected to a charging module, and the charging module may be but is not limited to being disposed on the circuit board 3. In this way, the wearable device may be charged through an electrical connection between an external charging device and the charging pin 7.

Figure 9:
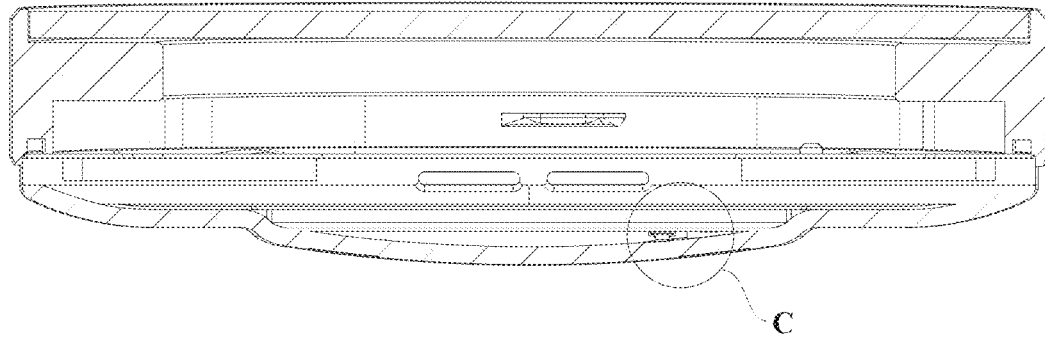
FIG. 9 is a cross-sectional view along B-B in FIG. 4.
Figure 10:
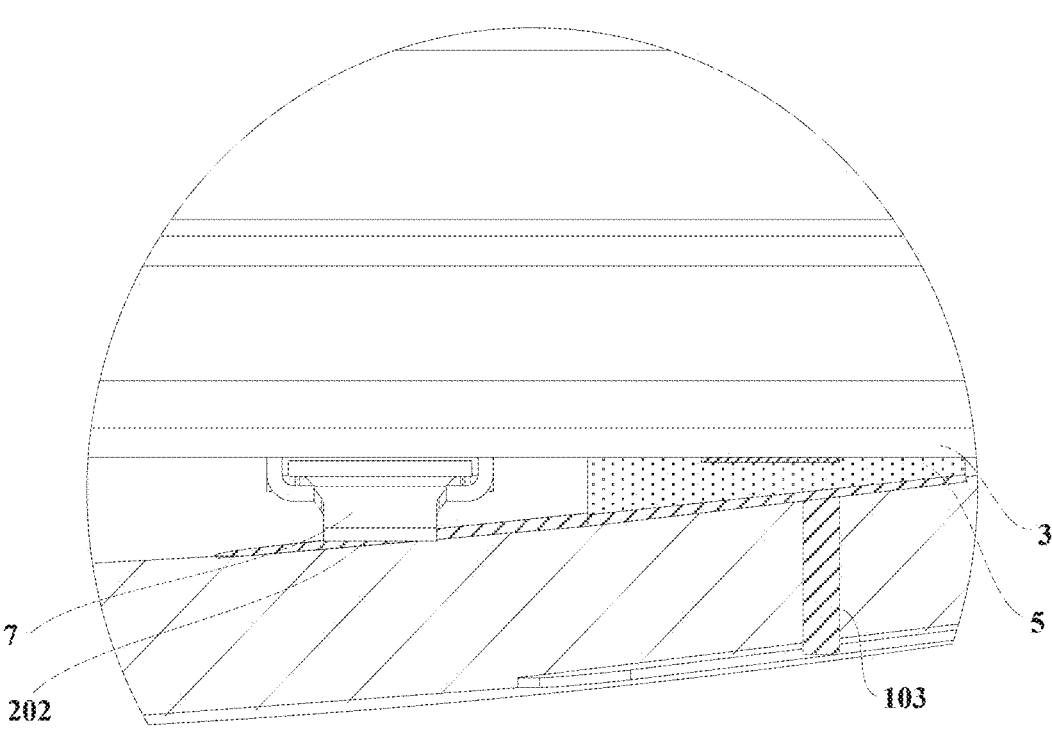
FIG. 10 is an enlarged view of a partial structure at C in FIG. 9.

FIG. 9 is a cross-sectional view along B-B in FIG. 4. In this application, the charging pin 7 may be fastened to the circuit board 3, and a fastening manner of the charging pin 7 may be but is not limited to welding, bonding, or the like. FIG. 10 is an enlarged view of a partial structure at C in FIG. 9. In this embodiment of this application, a length of the charging pin 7 may be designed, so that the charging pin 7 can be in direct contact with the second detection end 202 of the ECG electrode 2a, thereby effectively reducing a charging resistance of the wearable device and improving charging efficiency. In addition, to improve reliability of contact between the charging pin 7 and the second detection end 202, the charging pin 7 may be disposed as a spring, or the charging pin 7 is made of an elastic material, so that stable contact is implemented between the charging pin 7 and the second detection end 202 by using an elastic abutting force.

In a possible embodiment of this application, the charging pin 7 may be further electrically connected to the second detection end 202 of the ECG electrode 2a through a lead, and parameters such as a material and a thickness of the lead may be adjusted to reduce impedance. In some other embodiments of this application, the thermally and electrically conductive adhesive 5 may be further disposed between the charging pin 7 and the second detection end 202, and the second detection end 202 is connected to the charging pin 7 through the thermally and electrically conductive adhesive 5. It may be understood that the thermally and electrically conductive adhesive 5 may further have a bonding property. In this way, the charging pin 7 may be bonded and fastened to the circuit board 3 through the thermally and electrically conductive adhesive 5, to improve reliability of a connection between the charging pin 7 and the circuit board 3.

It may be understood that a connection manner between the charging pin 7 and the second detection end 202 provided in the foregoing embodiment is merely some example descriptions provided in this application. In some other possible embodiments of this application, another possible connection manner may be further used between the charging pin 7 and the second detection end 202, which is not listed herein, provided that a stable electrical connection between the charging pin 7 and the second detection end 202 can be implemented. It should be understood that the connection manner falls within the protection scope of this application.

In this application, the ECG electrode 2a is formed by using a material having a thermally and electrically conductive property, and the second detection end 202 of the ECG electrode 2a is electrically connected to the charging pin 7 on the circuit board 3. In this way, the first detection end 201 of the ECG electrode 2a may be electrically connected to the external charging device, so that a current generated by the external charging device enters the ECG electrode 2a through the first detection end 201, and is transmitted to the charging pin 7 through the second detection end 202 of the ECG electrode 2a. Then, the wearable device is charged by using a charging module that is in the circuit board 3 and that is electrically connected to the charging pin 7.

Currently, antenna modules (not shown in the figure) may further be disposed on some wearable devices, to implement wireless communication between the wearable device and another external terminal device. The antenna module may be electrically connected to a device in the wearable device to implement a function of the antenna. In addition, because the ECG electrode 2a has electrically conductive property, in some possible embodiments of this application, the antenna module may be disposed on the circuit board 3. In addition, the antenna module may be electrically connected, through the metal wire in the circuit board 3, to a contact exposed on a surface of the circuit board 3. For ease of differentiation, in this embodiment of this application, a contact electrically connected to the ECG module may be referred to as a first-type contact, and a contact electrically connected to the antenna module may be referred to as a second-type contact.

In this embodiment, the ECG electrode 2a may be electrically connected to the second-type contact on the circuit board 3, to integrate an antenna function into the ECG electrode 2a, so that the first detection end 201 of the ECG electrode 2a disposed on the first surface 1a of the first housing 1 receives or transmits an antenna signal. It may be understood that the ECG electrode 2a may be electrically connected to the second-type contact through, but not limited to, a structure that has a thermally and electrically conductive property, such as the thermally and electrically conductive adhesive 5, the lead, or the spring.

According to the wearable device provided in this embodiment of this application, the electrocardiogram detection, the body temperature detection, the charging function, and the antenna function may be integrated by using the ECG electrode 2a, thereby effectively saving the space for disposing the modules configured to implement the electrocardiogram detection, the body temperature detection, the charging function, and the antenna function. This helps implement the design for miniaturization and thinning of the wearable device. In addition, the electrocardiogram detection function, the body temperature detection function, and the charging function are integrated, so that space may be reserved for setting another functional module of the wearable device, thereby facilitating implementation of a design of diversified functions of the wearable device and improving user experience.

It may be understood from the descriptions of the disposing manner of the via 103 in the foregoing embodiment of this application that, in a possible implementation of this application, the via 103 may be disposed for implementing each corresponding function, so that the corresponding contact 4, temperature sensor 6, or charging pin 7 on the circuit board 3 is electrically connected to the corresponding via 103. In some other embodiments of this application, at least two functions may be implemented by disposing one via 103. In this case, an area of the second detection end 202 corresponding to the ECG electrode 2a of the via 103 may be set to be relatively large.

Figure 11:
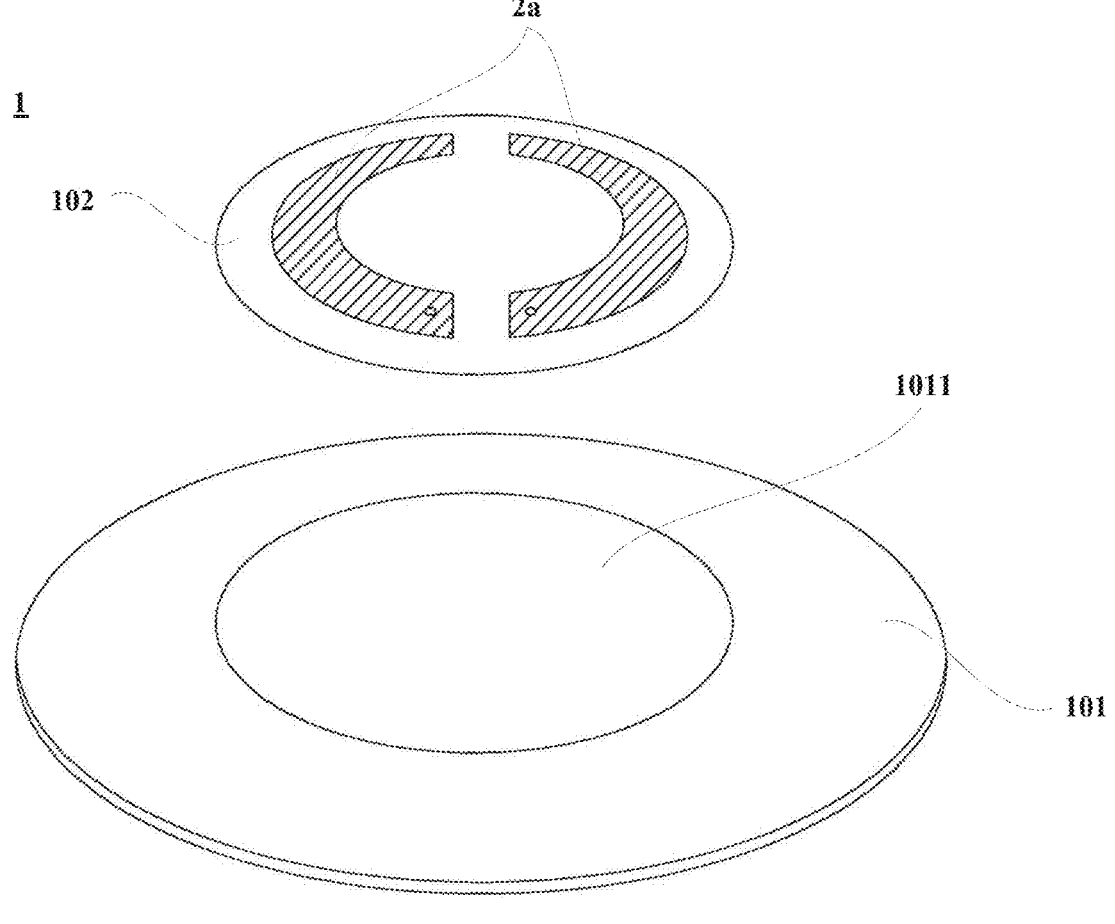
FIG. 11 is an exploded view of a first housing of a wearable device according to another embodiment of this application.

FIG. 11 is an exploded view of a first housing 1 of a wearable device according to another possible embodiment of this application. In this embodiment, the first housing 1 includes a fastening part 101 and a detection part 102. The fastening part 101 may be provided with a mounting hole 1011. For example, the fastening part 101 may be of an annular structure. The detection part 102 may be mounted in the mounting hole 1011 of the fastening part 101, and the detection part 102 is fastened to the fastening part 101. In this embodiment of this application, the fastening part 101 and the detection part 102 may be made of a same material or different materials. For example, the fastening part 101 may be made of plastic, ceramic, glass, or the like, and the detection part 102 may be made of plastic, ceramic, glass, or the like.

In this embodiment of this application, the ECG electrode 2a is disposed on the detection part 102, and the detection part 102 may protrude from the fastening part 101 towards a direction away from the accommodation space of the wearable device, to implement reliable contact between the ECG electrode 2a and the human body, thereby improving detection accuracy.

It may be understood that, for a specific disposing manner of another structure of the wearable device using the first housing 1 shown in FIG. 11 and a process of implementing the electrocardiogram detection function, the body temperature detection function, the charging function, and the antenna function, refer to any one of the foregoing embodiments. Details are not described herein again.

Figure 12:
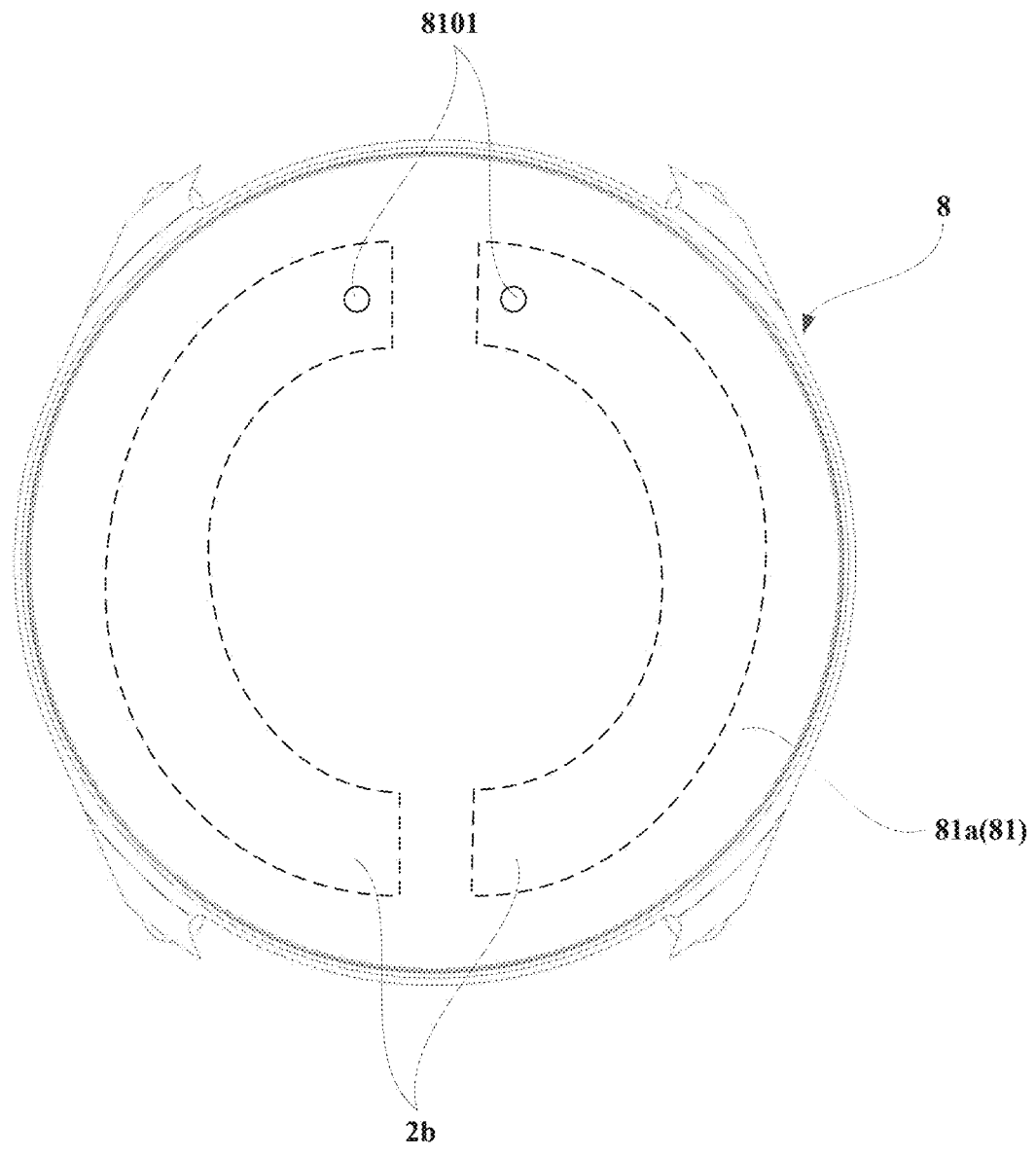
FIG. 12 is a schematic diagram of a structure of a wearable device according to another embodiment of this application.

In the foregoing embodiment of this application, the disposing manner of the ECG electrode 2a extending from the first surface 1a to the second surface 1b by opening the via 103 on the first housing 1 may be further used to dispose another structure of the wearable device in addition to the first housing 1. For example, it is known that the electrocardiogram detection usually needs to form a circulation loop that passes through a heart in the human body. Therefore, in addition to the ECG electrode 2a disposed in the first housing 1, an ECG electrode may be disposed in an area that can still be touched after the wearable device is worn on the human body. For example, FIG. 12 shows a structure of a second housing 8 of a wearable device according to an embodiment of this application. In this embodiment, an ECG electrode 2b may be disposed on the second housing 8 of the housing of the wearable device. A smart watch is still used as an example of the wearable device. When the smart watch is worn on a left hand of the human body, the ECG electrode 2a disposed on the first housing 1 may be in contact with the left hand, and a right hand of the human body may be in contact with the ECG electrode 2b disposed on the second housing 8, so that an electrocardiogram detection path may be formed.

The second housing 8 of the wearable device may include a display 81, and the display 81 may be configured to display detection results such as an electrocardiogram and a body temperature, and a power level, a signal state, or the like of the wearable device, so that the user can intuitively learn of a health state of the user and a working state of the wearable device. In a possible embodiment of this application, the ECG electrode 2b may be disposed in a display area of the display 81 of the second housing 8. In this case, the ECG electrode 2b may be made of a transparent material that has a thermally and electrically conductive property. In some other possible embodiments of this application, the ECG electrode 2b may be further disposed in a non-display area of the display 81 of the second housing 8. In this case, there is no requirement on transparency of a material of the ECG electrode 2b, provided that the material has a relatively good thermal and electrically conductive property.

Figure 13:
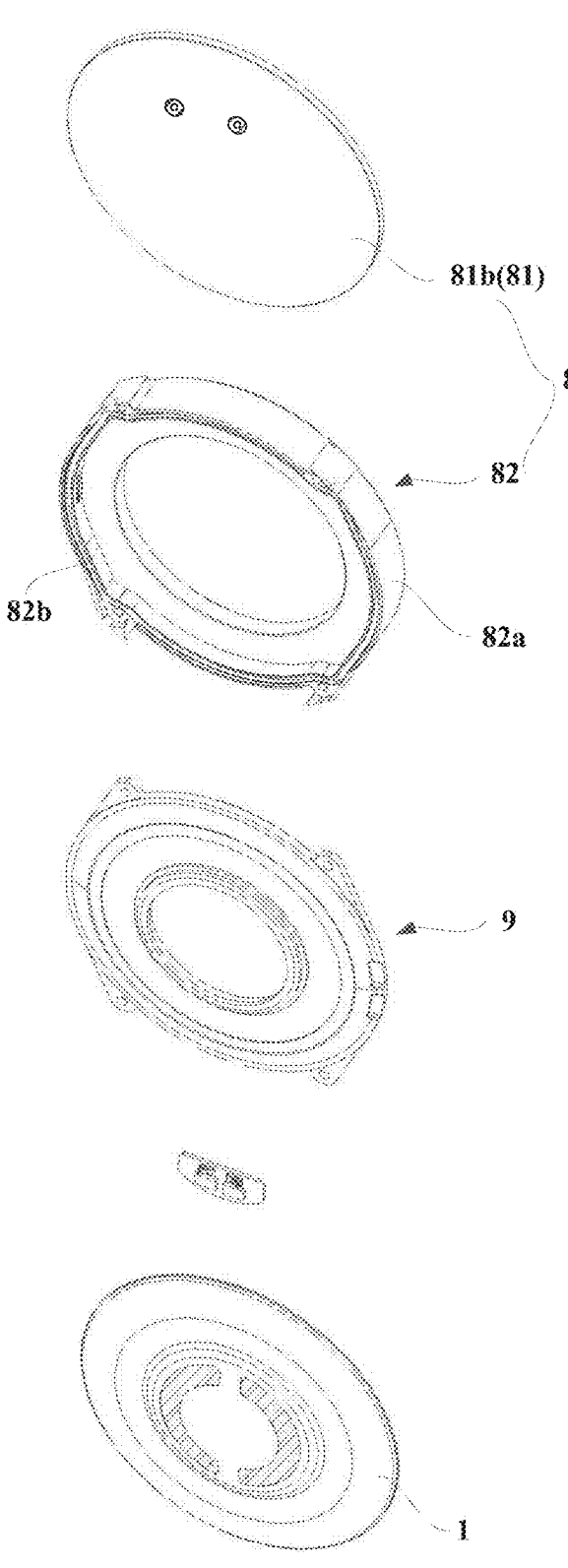
FIG. 13 is an exploded view of a wearable device according to another embodiment of this application.

FIG. 13 shows an exploded view of the wearable device shown in FIG. 12. In a possible embodiment of this application, a side surface that is of the display 81 of the second housing 8 and that is used for display may be defined as a first surface 81a of the display 81, and a side surface that is of the display 81 and that faces the accommodation space is defined as a second surface 81b of the display 81. A via 8101 is also disposed on the display 81, and the via 8101 penetrates the display 81 in a direction from the first surface 81a to the second surface 81b. In this case, the ECG electrode 2b may extend from the first surface 81a of the display 81 to the second surface 81b of the display 81 through the via 8101, so that the ECG electrode 2b is connected to a circuit board located in the accommodation space.

It may be understood that, for a connection between the ECG electrode 2b of the display 81 disposed on the second housing 8 and the circuit board, refer to the foregoing connection manner between the ECG electrode 2a of the first housing 1 and the circuit board 3 in the embodiment shown in FIG. 7. For example, the contact 4 and the like may be formed on the circuit board, and details are not described herein. In addition, the ECG electrode 2b on the display 81 and the ECG electrode 2a on the first housing 1 may be electrically connected to a same circuit board 3, or may be electrically connected to different circuit boards 3. The ECG electrode 2b and the ECG electrode 2a may be designed based on a specific layout manner in the accommodation space of the wearable device.

Similar to the first housing 1, the ECG electrode 2b disposed on the display 81 may also be formed by using a thermally and electrically conductive material. In this way, the ECG electrode 2b may also be connected, through a structure that has a thermally and electrically conductive property such as a thermally and electrically conductive adhesive, a lead, or a spring, to the temperature sensor disposed on the circuit board, to detect an ambient temperature by using the ECG electrode 2b. In this solution, an electrocardiogram detection function and an ambient temperature detection function may be integrated by using the ECG electrode 2b disposed on the second housing 8. In this solution, when the ambient temperature detection function is added to the wearable device, excessive space occupation of the wearable device can be avoided. In this way, impact on a miniaturization design of the wearable device is relatively small, and user experience can be improved. In addition, the body temperature detected by the ECG electrode 2a of the first housing 1 may be further calibrated based on the ambient temperature detected by the ECG electrode 2b, to improve accuracy of the body temperature detection.

Figure 14:
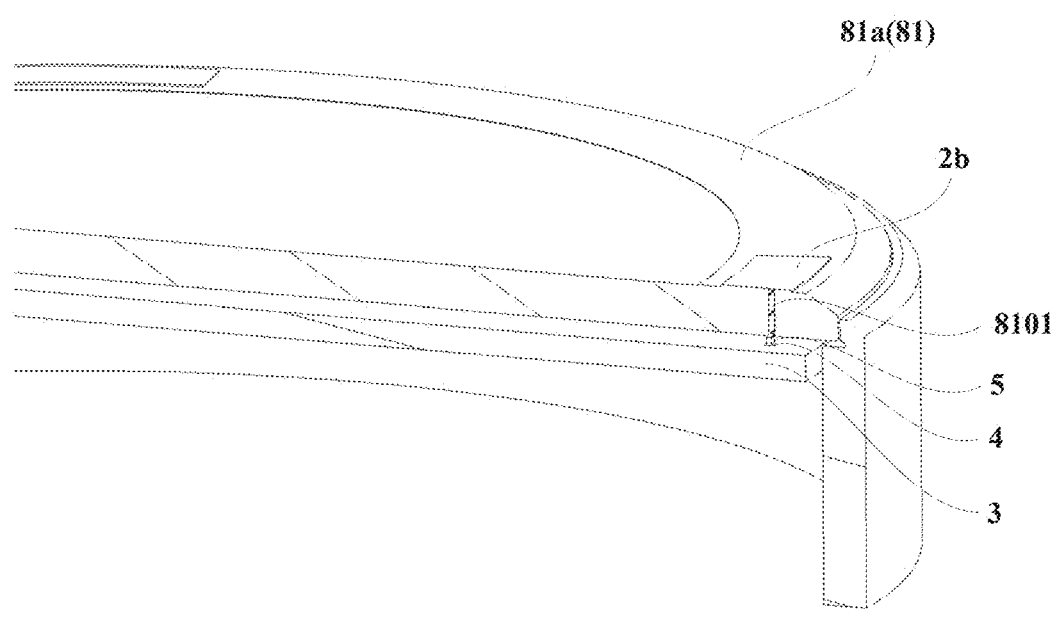
FIG. 14 is a schematic diagram of a partial structure of a wearable device according to an embodiment of this application.

It may be understood that when the wearable device is worn on the user, the display 81 may be always exposed. Based on this, in this application, the antenna function of the wearable device may also be integrated into the ECG electrode 2b of the display 81, to provide more choices for the user. In specific implementation, refer to FIG. 14. FIG. 14 is a schematic diagram of a partial structure of a wearable device according to a possible embodiment of this application. In FIG. 14, the ECG electrode 2b extends from the first surface 81a of the display 81 to the second surface 81b (referring to FIG. 13) of the display 81, and the contact 4 on the circuit board 3 includes the second-type contact. In addition, the antenna module (not shown in the figure) is disposed on the circuit board 3, and the second-type contact is electrically connected to the antenna module. In this embodiment of this application, a part that is of the ECG electrode 2b and that is located on the second surface 81b may be electrically connected to the second-type contact through the thermally and electrically conductive adhesive 5, so that an antenna signal may be received or transmitted by using a part that is of the ECG electrode 2b and that is disposed on the first surface 81a of the display, to implement the antenna function of the wearable device.

It should be noted that the part that is of the ECG electrode 2b and that is located on the second surface 81b may be electrically connected to the second-type contact through a structure having a thermally and electrically conductive property, such as a lead or a spring. In addition, in the embodiment shown in FIG. 14, the charging function of the wearable device may be further integrated into the ECG electrode 2b by disposing the charging pin on the circuit board 3. For a specific disposing manner, refer to the foregoing embodiment. Details are not described herein again.

Still with reference to FIG. 13, in this embodiment of this application, the second housing 8 may further include a support 82. The support 82 is located on a side that is of the display 81 and that faces the accommodation space. The display 81 may be fastened to the support 82, so that the support 82 supports the display 81. A material of the support 82 may be but is not limited to metal, plastic, or the like. In addition, in this application, to implement fastening of the first housing 1, the wearable device may further include a mounting bracket 9. The mounting bracket 9 may be located on a side that is of the first housing 1 and that faces the accommodation space of the wearable device, and the first housing 1 is fastened to the mounting bracket 9. A material of the mounting bracket 9 may be but is not limited to metal, plastic, or the like, to reliably support the first housing 1. In addition, the support 82 and the mounting bracket 9 may be connected in a fastening manner by using a fastener, but not limited to a fastener.

In this application, the support 82 may be disposed in an annular structure, so that the support 82 is used as a part of the housing of the wearable device. The support 82 has a side wall, and the side wall may be configured to connect the first housing 1 and the display 81, so that the side wall, the first housing 1, and the display 81 jointly form enclosed accommodation space. When the wearable device is worn on the human body, because the side wall also has a touchable area, in some possible embodiments of this application, the ECG electrode may also be disposed in the touchable area of the side wall of the support 82.

Figure 15:
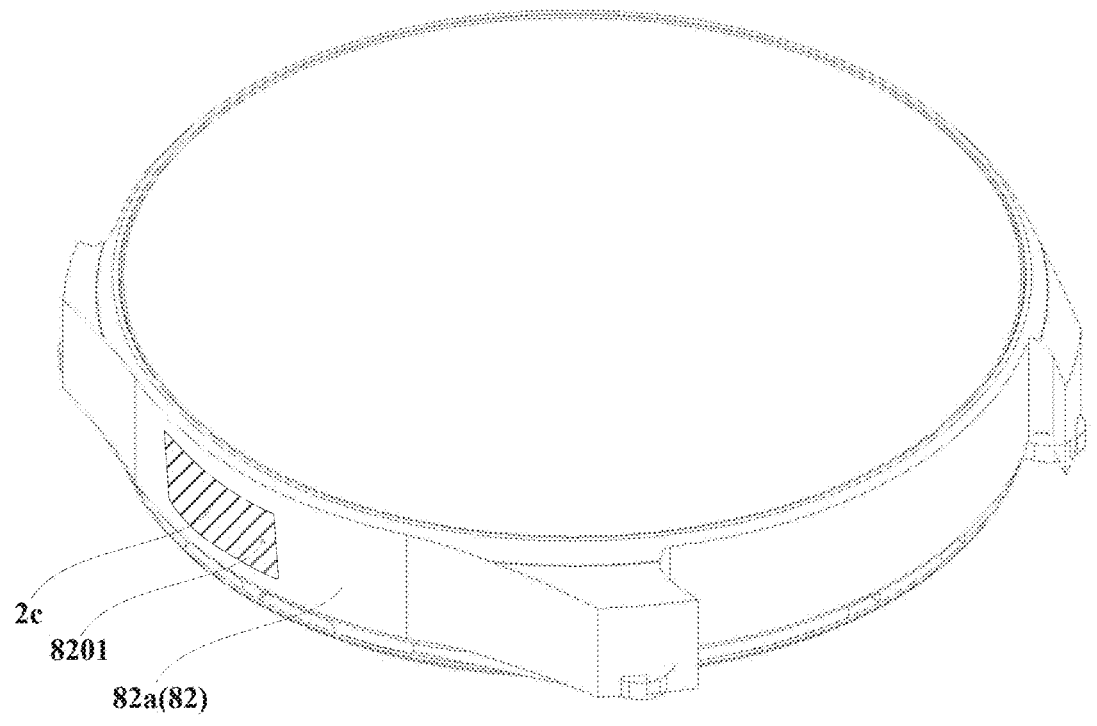
FIG. 15 is a perspective view of a wearable device according to an embodiment of this application.

FIG. 15 is a perspective view of the wearable device shown in FIG. 13. In this embodiment of this application, a side surface that is of the side wall of the support 82 and that can be seen by the user may be defined as a first surface 82a of the side wall, and a side surface that is of the side wall and that faces the accommodation space is defined as a second surface 82b of the side wall. In addition, a via 8201 may also be disposed on the side wall. The via 8201 penetrates the side wall of the support 82 in a direction from the first surface 82a of the side wall to the second surface 82b of the side wall. In this case, an ECG electrode 2c may extend from the first surface 82a of the side wall of the support 82 to the second surface 82b of the side wall of the support 82 through the via 8201, so that the ECG electrode 2c is electrically connected to the circuit board located in the accommodation space.

It may be understood that, in this embodiment, a specific disposition position, a shape, and the like of the ECG electrode 2c on the side wall of the support 82 are not limited, and the ECG electrode 2c may be adaptively adjusted based on a side wall structure of the support 82. In addition, the ECG electrode 2c disposed on the side wall of the support 82 may also be formed by using a transparent material that has a thermally and electrically conductive property, to improve appearance aesthetics of the wearable device.

In the embodiment shown in FIG. 15, for a connection between the ECG electrode 2c disposed on the side wall of the support 82 and the circuit board, refer to a connection manner between the ECG electrode 2a of the first housing 1 and the circuit board 3 in any one of the foregoing embodiments. For example, the contact 4 and the like may be formed on the circuit board 3. Details are not described herein.

Similar to the first housing 1, the ECG electrode 2c disposed on the side wall of the support 82 may also be formed by using a thermally and electrically conductive material. In this way, the ECG electrode 2c may also be connected, through the thermally and electrically conductive adhesive, to the temperature sensor disposed on the circuit board, to detect the ambient temperature by using the ECG electrode 2c. In this solution, the electrocardiogram detection function and the ambient temperature detection function may be integrated by using the ECG electrode 2c disposed on the side wall of the support 82. In this solution, when the ambient temperature detection function is added to the wearable device, excessive space occupation of the wearable device can be avoided. In this way, impact on a miniaturization design of the wearable device is relatively small, and user experience can be improved. In addition, the body temperature detected by the ECG electrode 2a of the first housing 1 may be further calibrated based on the ambient temperature detected by the ECG electrode 2c, to improve accuracy of the body temperature detection.

It may be understood that, on the basis of the foregoing embodiment, the charging function and the antenna function of the wearable device may also be integrated into the ECG electrode 2c on the side wall of the support 82 through proper design, to provide more choices for the user.

It should be noted that, by using the wearable device provided in this application, ECG electrodes may be disposed in any two structures of the first housing 1, the display 81, and the support 82 to implement the electrocardiogram detection. In addition, when the ECG electrodes are disposed in the three structures of the first housing 1, the display 81, and the support 82, a plurality of electrocardiogram detection channels may be formed through proper design. The plurality of electrocardiogram detection channels may be mutually calibrated, to improve accuracy of the electrocardiogram detection performed by the wearable device.

According to the wearable device provided in this application, an ECG electrode may be disposed on a structure such as the first housing 1, the display 81, the support 82, and the like, and the ECG electrode is formed by using a thermally and electrically conductive material, so that the electrocardiogram detection, the body temperature detection, the charging function, the antenna function, and the like are integrated by using the ECG electrode, to implement a design for miniaturization and thinning of a structure of the wearable device. In addition, the via is disposed on the structure on which the ECG electrode is disposed, so that the ECG electrode formed on a side surface of the structure extends, through the via, to a side surface that is of the structure and that is located in the accommodation space, thereby facilitating an electrical connection between the ECG electrode and another device in the accommodation space of the wearable device, and effectively improving aesthetics of an ECG electrode area disposed on the wearable device.

It may be understood that the solution provided in this application for integrating a plurality of functions by using the ECG electrode may be disposed in the wearable device, and may be further applied to another possible electronic device. For example, the solution may be used in a mobile phone, a stereo, a television, a vacuum cleaning robot, a router, or the like, to dispose an ECG electrode on a housing of the electronic device in the foregoing manner, and integrate an electrocardiogram detection function, a body temperature detection function, a charging function, an antenna function, and the like by using the ECG electrode. This can implement a design for miniaturization and thinning of the electronic device. In addition, space may be reserved for disposing another functional module, to implement function diversity of the electronic device.

The foregoing descriptions are merely specific implementations of this application, but are not intended to limit the protection scope of this application. Any variation or replacement readily figured out by a person skilled in the art within the technical scope disclosed in this application shall fall within the protection scope of this application. Therefore, the protection scope of this application shall be subject to a protection scope of the claims.

The invention claimed is:

1. A wearable device, comprising a first housing, a second housing, a first electrocardiograph (ECG) electrode, a circuit board, and a temperature sensor, wherein:

a material of the first housing is one or more of ceramic, glass, or plastic;

the first housing and the second housing are disposed in a snap-fit manner to form accommodation space between the first housing and the second housing;

the first housing comprises a first surface, a second surface, and a first via, the second surface faces the accommodation space, the first surface and the second surface are disposed back to each other, and the first via penetrates the first housing in a direction from the first surface to the second surface;

the first ECG electrode comprises a first detection end, a second detection end, and a connection part, the first detection end is disposed on the first surface of the first housing, the second detection end is disposed on the second surface of the first housing, the connection part penetrates the first via, and the first detection end is connected to the second detection end through the connection part; and the circuit board is disposed in the accommodation space, a contact and the temperature sensor are disposed on the circuit board, the second detection end is electrically connected to the contact, and the second detection end is in thermally conductive contact with the temperature sensor.

2. The wearable device according to claim 1, wherein the first ECG electrode comprises a substrate and silicon carbide or silver doped on the substrate.

3. The wearable device according to claim 1, wherein a thermally and electrically conductive adhesive is disposed between the circuit board and the second detection end, the second detection end is electrically connected to the contact through the thermally and electrically conductive adhesive, and the second detection end is in thermally conductive contact with the temperature sensor through the thermally and electrically conductive adhesive.

4. The wearable device according to claim 1, wherein the contact comprises a first-type contact, an ECG module is disposed on the circuit board, and the first-type contact is electrically connected to the ECG module.

5. The wearable device according to claim 1, wherein a charging pin is further disposed on the circuit board, and the charging pin is electrically connected to the second detection end.

6. The wearable device according to claim 5, wherein a charging module is further disposed on the circuit board, and the charging pin is electrically connected to the charging module.

7. The wearable device according to claim 1, wherein the first housing is an integrally formed structure.

8. The wearable device according to claim 1, wherein the first housing comprises a fastening part and a detection part, the fastening part is provided with a mounting hole, the detection part is mounted in the mounting hole, the detection part is fastened to the fastening part, and the first ECG electrode is disposed on the detection part.

9. The wearable device according to claim 1, wherein:

the second housing comprises a display, the display has a first surface, a second surface, and a second via, the first surface of the display and the second surface of the display are disposed back to each other, the second surface of the display faces the accommodation space, and the second via penetrates the display in a direction from the first surface of the display to the second surface of the display; and a second ECG electrode is disposed on the display, the second ECG electrode passes through the second via and extends from the first surface of the display to the second surface of the display, a first part that is of the second ECG electrode and that is located on the first surface of the display is electrically connected to a second part that is of the second ECG electrode and that is located on the second surface of the display, and the second part is electrically connected to the circuit board.

10. The wearable device according to claim 9, wherein the contact comprises a second-type contact, an antenna module is disposed on the circuit board, the second-type contact is electrically connected to the antenna module, and the second ECG electrode is electrically connected to the second-type contact.

11. The wearable device according to claim 9, wherein:

the second housing further comprises a support, the support is located on a side that is of the display and that faces the accommodation space, the support has a side wall configured to connect the first housing and the display, the side wall comprises a first surface, a second surface, and a third via, the first surface of the side wall and the second surface of the side wall are disposed back to each other, the second surface of the side wall faces the accommodation space, and the third via penetrates the side wall in a direction from the first surface of the side wall to the second surface of the side wall; and a third ECG electrode is disposed on the side wall of the support, the third ECG electrode passes through the third via and extends from the first surface of the side wall to the second surface of the side wall, a third part that is of the third ECG electrode and that is located on the first surface of the side wall is electrically connected to a fourth part that is of the third ECG electrode and that is located on the second surface of the side wall, and the fourth part is electrically connected to the circuit board.

12. The wearable device according to claim 11, wherein the contact comprises a second-type contact, an antenna module is disposed on the circuit board, the second-type contact is electrically connected to the antenna module, and the third ECG electrode is electrically connected to the second-type contact.

* * * * *